United States Patent
Delamarche et al.

(10) Patent No.: US 10,369,567 B2
(45) Date of Patent: Aug. 6, 2019

(54) CONTINUOUS, CAPACITANCE-BASED MONITORING OF LIQUID FLOWS IN A MICROFLUIDIC DEVICE

(71) Applicant: INTERNATIONAL BUSINESS MACHINES CORPORATION, Armonk, NY (US)

(72) Inventors: Emmanuel Delamarche, Rueschlikon (CH); Yuksel Temiz, Rueschlikon (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 122 days.

(21) Appl. No.: 14/932,393

(22) Filed: Nov. 4, 2015

(65) Prior Publication Data
US 2017/0120240 A1    May 4, 2017

(51) Int. Cl.
*B01L 3/00* (2006.01)
*G01N 27/22* (2006.01)
*G01F 1/56* (2006.01)
*G01F 22/00* (2006.01)

(52) U.S. Cl.
CPC ..... *B01L 3/50273* (2013.01); *B01L 3/502715* (2013.01); *G01N 27/22* (2013.01); *B01L 2200/027* (2013.01); *B01L 2200/0605* (2013.01); *B01L 2200/0621* (2013.01); *B01L 2200/143* (2013.01); *B01L 2300/0645* (2013.01); *B01L 2300/0816* (2013.01);
(Continued)

(58) Field of Classification Search
CPC .......... B01L 3/50273; B01L 3/502715; B01L 2200/027; B01L 2200/145; B01L 2300/0645; B01L 2300/0816; B01L 2300/0861; B01L 2400/0406; G01N 27/22; G01N 27/226; C12Q 2565/629; C12Q 2565/607
See application file for complete search history.

(56) References Cited

U.S. PATENT DOCUMENTS 6,212,956 B1 * 4/2001 Donald ............... G01N 27/221
                                                73/724
6,437,551 B1    8/2002 Krulevitch et al.
(Continued)

FOREIGN PATENT DOCUMENTS

CN    103249486 A    8/2013
CN    103323502 A    9/2013
(Continued)

OTHER PUBLICATIONS

International Search Report, dated Jan. 26, 2017, pp. 1-13.

*Primary Examiner* — Son T Le
*Assistant Examiner* — Dustin R Dickinson
(74) *Attorney, Agent, or Firm* — Cantor Colburn LLP; Daniel Morris

(57) ABSTRACT

A microfluidic chip comprising a microchannel fillable with a liquid, the microchannel comprises a pair of electrodes, and a liquid flow path defined between the electrodes, wherein each of the electrodes extends along the flow path and parallel to a direction of a liquid filling the microchannel, in operation, and an electrical circuitry connected to each of the electrodes and configured to continuously measure, via the electrodes, a capacitance of the electrodes being wet by a liquid continuously filling the flow path, as a function of time, in operation.

22 Claims, 6 Drawing Sheets

(52) U.S. Cl.
CPC .................. *B01L 2300/0861* (2013.01); *B01L 2400/0406* (2013.01); *G01F 1/56* (2013.01); *G01F 22/00* (2013.01)

(56) References Cited

U.S. PATENT DOCUMENTS

| | | | | |
|---|---|---|---|---|
| 8,252,159 | B2* | 8/2012 | Roux | B01L 3/50273 |
| | | | | 204/450 |
| 8,872,527 | B2 | 10/2014 | Sturmer et al. | |
| 2003/0226604 | A1* | 12/2003 | Schlautmann | B01L 3/502707 |
| | | | | 137/827 |
| 2004/0242982 | A1* | 12/2004 | Sakata | A61B 5/14532 |
| | | | | 600/345 |
| 2005/0042766 | A1* | 2/2005 | Ohman | B01L 3/50273 |
| | | | | 436/174 |
| 2005/0047968 | A1* | 3/2005 | Kido | B01L 3/50273 |
| | | | | 422/400 |
| 2005/0092606 | A1 | 5/2005 | Reich et al. | |
| 2005/0243860 | A1* | 11/2005 | Chen | H04W 48/18 |
| | | | | 370/465 |
| 2006/0054226 | A1* | 3/2006 | Yamazaki | B01L 3/502738 |
| | | | | 137/827 |
| 2006/0188403 | A1 | 8/2006 | Query | |
| 2007/0238112 | A1 | 10/2007 | Sohn et al. | |
| 2010/0137163 | A1 | 6/2010 | Link et al. | |
| 2010/0233824 | A1* | 9/2010 | Verhoeckx | B01L 3/502715 |
| | | | | 436/501 |
| 2010/0261286 | A1* | 10/2010 | Kim | B01L 3/502707 |
| | | | | 436/149 |
| 2011/0011781 | A1* | 1/2011 | Blankenstein | B01L 3/502715 |
| | | | | 210/205 |
| 2012/0206384 | A1* | 8/2012 | Marsden | G06F 3/023 |
| | | | | 345/173 |
| 2013/0183209 | A1* | 7/2013 | Richter | A61M 5/16827 |
| | | | | 422/403 |
| 2015/0204817 | A1* | 7/2015 | Jansson | F04B 19/006 |
| | | | | 204/450 |

FOREIGN PATENT DOCUMENTS

| | | |
|---|---|---|
| JP | 2010188265 A | 9/2010 |
| KR | 100807852 B1 | 2/2008 |
| WO | 2010095577 A1 | 8/2010 |

* cited by examiner

US 10,369,567 B2

CONTINUOUS, CAPACITANCE-BASED MONITORING OF LIQUID FLOWS IN A MICROFLUIDIC DEVICE

BACKGROUND

The invention relates in general to the field of microfluidics and in particular to microfluidic chips equipped with electrodes to perform measurements on liquids in the chip, such as microfluidics for point-of-care diagnostics, as well as related systems and flow monitoring methods.

Microfluidics deals with the behavior, precise control and manipulation of small volumes of fluids that are typically constrained to micrometer-length scale channels and to volumes typically in the sub-milliliter range. Prominent features of microfluidics originate from the peculiar behavior that liquids exhibit at the micrometer length scale. Flow of liquids in microfluidics is typically laminar. Volumes well below one nanoliter can be reached by fabricating structures with lateral dimensions in the micrometer range. Reactions that are limited at large scales (by diffusion of reactants) can be accelerated. Finally, parallel streams of liquids can possibly be accurately and reproducibility controlled, allowing for chemical reactions and gradients to be made at liquid/liquid and liquid/solid interfaces.

More in detail, typical volumes of fluids in microfluidics range from $10^{-15}$ L to $10^{-4}$ L and are transported, circulated or more generally moved via channels (or microchannels) having a typical diameter of $10^{-7}$ m to $10^{-4}$ m. At the microscale, the behavior of fluids can differ from that at a larger, e.g., macroscopic, scale, such that surface tension, viscous energy dissipation and fluidic resistance may become dominant characteristics of the fluid flow. For instance, in microfluidics, the Reynolds number, which compares the effects of fluid momentum and viscosity, may decrease to such an extent that the flow behavior becomes laminar rather than turbulent.

In addition, at the microscale, fluids do not necessarily chaotically mix as at the microscale due to absence of turbulence in low Reynolds number flows, and interfacial transport of molecules or small particles between adjacent fluids often takes place through diffusion. As a consequence, certain chemical and physical fluid properties (such as concentration, pH, temperature and shear force) may become deterministic. This makes it possible to obtain more uniform chemical reaction conditions and higher-grade products in single and multi-step reactions.

Microfluidic devices generally refer to microfabricated devices, which are used for pumping, sampling, mixing, analyzing and dosing liquids. The majority of microfluidic devices are sealed and have inlets/outlets for pumping in and out liquids through them. Some microfluidic devices such as the so-called "microfluidic probes", however, can scan surfaces and localize liquids on selected areas of surfaces without the need for sealing the flow paths.

Microfluidic devices for point-of-care diagnostics are devices meant to be used by non-technical staff, near patients or in the field, and potentially at home. Existing point-of-care devices typically require loading a sample onto the device and waiting a predefined time until a signal (usually optical or fluorescence signal) can be read. The signal originates from (bio)chemical reactions and relates to the concentration of an analyte in a sample. These reactions take times and are difficult to implement because they require optimal timing, flow conditions of sample and accurate dissolution of reagents in the device. The reactions involve fragile reagents such as antibodies. Air bubbles may be created in the device, which can invalid tests. In addition, debris in a device can block liquid flows. In devices where liquids must be split in parallel flow paths, filling may not occur at the same flow rate and this can bias or invalidate the tests. In addition, some tests fail due to manufacturing problems.

Moreover, microfluidic devices for point-of-care diagnostics are typically non-transparent (to protect reagents from light) and are usually too small to allow optical flow monitoring, which would require bulky and expensive optical systems and/or advanced image processing algorithms Instead of using active pumping means, microfluidic devices are known, which use capillary forces for moving a liquid sample inside the microfluidic device. This makes the device simpler to operate and less expensive because there is no need for integrated or external pump. However, particulates, contamination and other issues during manufacture can compromise capillary-based filling of the device.

SUMMARY

According to an embodiment of the present invention, a microfluidic chip comprising a microchannel fillable with a liquid, the microchannel comprises a pair of electrodes, and a liquid flow path defined between the electrodes, wherein each of the electrodes extends along the flow path and parallel to a direction of a liquid filling the microchannel, in operation, and an electrical circuitry connected to each of the electrodes and configured to continuously measure, via the electrodes, a capacitance of the electrodes being wet by a liquid continuously filling the flow path, as a function of time, in operation.

According to another embodiment of the present invention,

BRIEF DESCRIPTION OF THE DRAWINGS

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

As outlined in introduction, the filling of microfluidic devices for point-of-care diagnostics is critical; it can sometimes go wrong. This, in the worst case, may result in a wrong diagnostic. In the best case, a failure in filling of a device requires to redo the test with another device. As present inventors have realized, it would be advantageous to be able to continuously monitor a liquid as it fills a microchannel of such a device, in order to warn a user as soon as possible if something goes wrong.

As further evoked in introduction, some microfluidic devices are known, which use electrodes placed across the microchannels for detecting the presence of a liquid in the vicinity of the electrodes, e.g., using capacitive measurements. However, it can be realized that spreading a few pairs of electrodes to create checkpoints for liquid filling is insufficient for accurately tracking the filling status of a microfluidic device. Indeed, there are too many potential failure points for filling; a reduced set of electrodes can even be misleading by suggesting that filling proceeded appropriately whereas filling can fail after the last pair of electrodes. As it can be realized too, multiplying the number of pairs of electrodes is not a viable option because each electrode requires a separate contact pad. More pads require more space and result in a larger device. Such a device would eventually lose in portability and be more expensive to manufacture.

As present inventors have realized too, there is a more general need for monitoring the flow of minutes quantities of liquids. Indeed, microfluidic devices deal with only microliters of sample and flow rates in these devices can be as small as 1 nanoliter per second or less. A high-accuracy in monitoring flow would therefore be highly advantageous, even though this cannot be achieved with transverse electrodes.

Having made the above observations, the present inventors designed devices and systems relying on continuous capacitance measurements, via longitudinal electrodes, where a capacitance of the electrodes changes as they are being wet by a liquid continuously filling a flow path of a microchannel. This, as well as preferred embodiments of the invention, is explained in detail below. The following description is structured as follows. First, general embodiments and high-level variants are described (sect. 1). The next sections address specific embodiments and technical implementation details (sect. 2 and 3).

Figure 2:
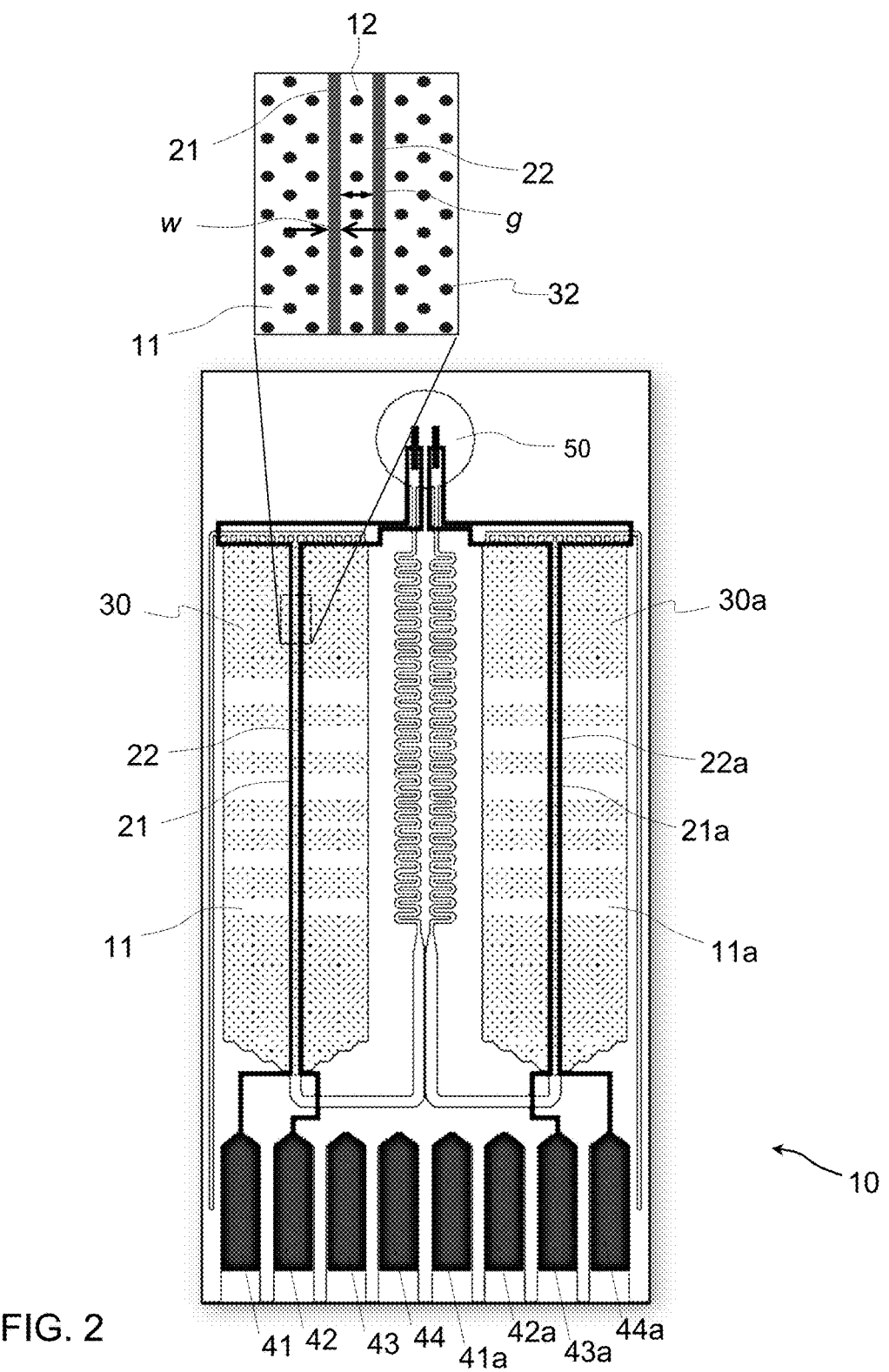
FIG. 2 is a top view of a microfluidic chip comprising longitudinal electrodes and electrical circuitry connected thereto, for performing continuous capacitance measurements, according to embodiments.
Figure 4:
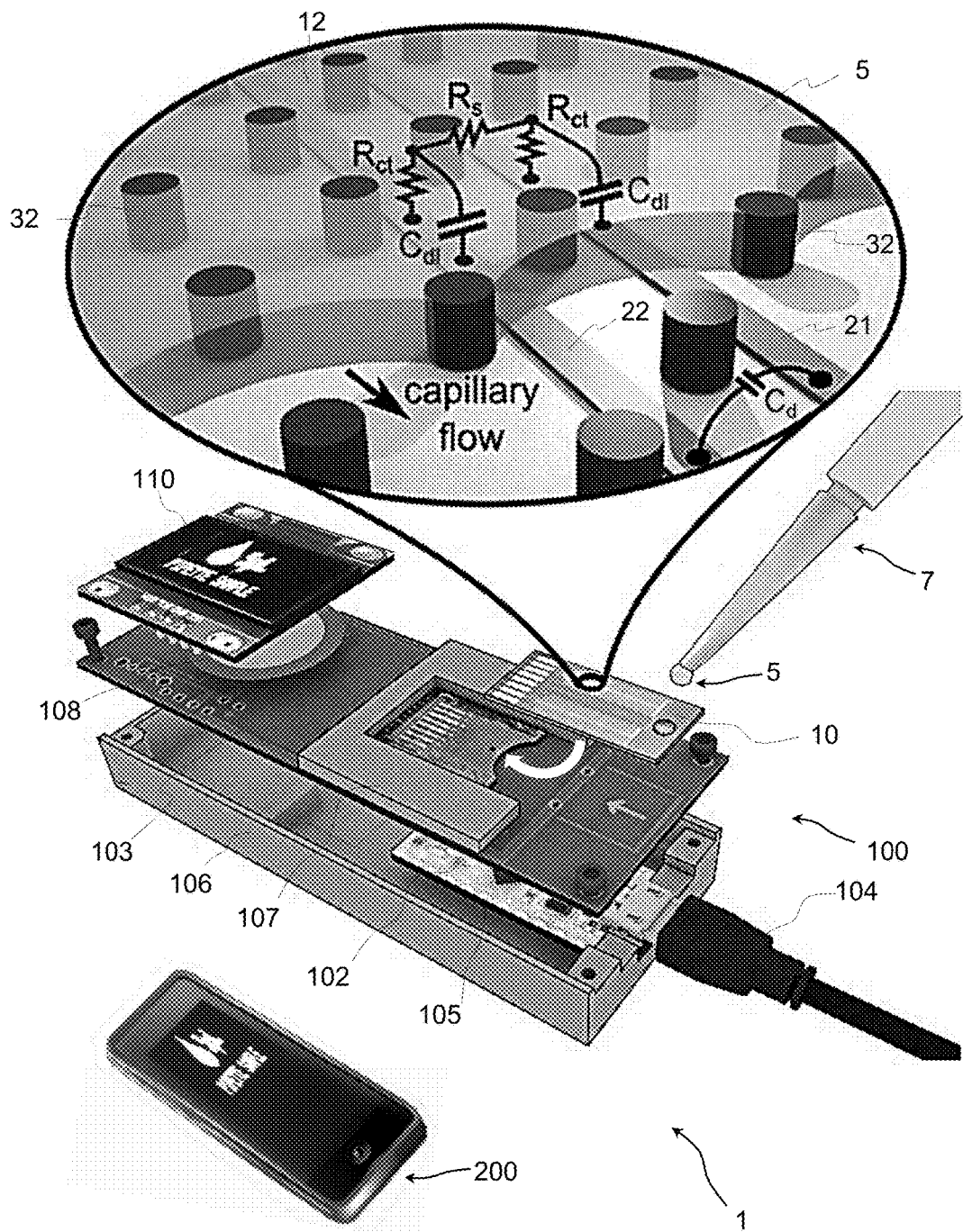
FIG. 4 shows an exploded view of a flow monitoring device, as involved in a system according to embodiments, which may further comprise a mobile device. The inset shows details of the microchannel surface and a liquid front advancing across a lattice of capillary structures.

In reference to FIGS. 2 and 4, an aspect of the invention is first described, which concerns a microfluidic chip 10. The latter notably comprises a microchannel 11 (or a microchannel portion) that can be filled with a liquid 5. The microchannel 11 comprises a pair of electrodes 21, 22 and a liquid flow path 12 defined between the electrodes 21, 22. Each of the electrodes 21, 22 extends along the flow path and parallel to the direction (vertical, upwards, in FIG. 2) of the liquid as the latter fills the microchannel, in operation.

In addition, an (on-chip) electrical circuitry is provided, which is connected to each of the electrodes 21, 22. The circuitry may notably comprise electrical connectors 41-44a, appropriately connected to the electrodes, to convey electrical signals to a processing unit, which will be described later. The on-chip circuitry is generally configured so as to be able to continuously measure, via the electrodes 21, 22, a capacitance of the electrodes as the latter get wet by a liquid 5 that continuously fills the flow path 12, as a function of time.

The electrodes 21, 22 are longitudinal electrodes. I.e., they extend longitudinally, on each side of the flow path 12 defined between the electrodes 21, 22. By "longitudinal" electrodes 21, 22, it is hereafter meant electrodes extending along the flow path (as opposed to transverse electrodes), i.e., parallel to a direction of the liquid 5 when the latter fills the flow path and irrespective of the actual shape of the channel (which can be a straight channel, as in the example of FIG. 2, or not). Using longitudinal electrodes 21, 22 allows the liquid 5 progression to be continuously monitored, in operation, which in turn allows relevant feedback (e.g., indications) to be timely provided to the user manipulating the chip 10, as discussed below in detail.

"Continuously measure" means repeatedly measure the changing capacitance, at a frequency that typically is between 1 ms and 1 s. As explained later in reference to FIGS. 5-7, the frequency depends on the RC time constant, which may, in the present context, lead to measurement frequencies between 1 Hz and 1 kHz, depending on the fixed resistor and the measured capacitance. Considering that the liquid flow is usually slow in a chip such as represented in FIG. 2, a few measurements per second is already typically sufficient to reasonably estimate a liquid flow rate.

In embodiments such as depicted in FIG. 2, the microfluidic chip 10 comprises in fact two microchannels 11, 11a, where each microchannel comprises a pair of electrodes 21, 22; 21a, 22a and a liquid flow path is defined between each pair of electrodes. Each pair of electrodes extend along the flow path and parallel to the direction of the liquid 5, in operation. The electrical circuitry is connected to each pair of electrodes, so as to enable capacitance measurements via each pair of electrodes.

The same concept can be scaled up to more independent channels, if needed. Using several channels allows to average measured values and thereby obtain measurements that are more accurate. In addition, using several channels allows for multiplexed assays, where each channel may have a different flow rate, optimized for a different analyte, where each channel can be individually monitored.

Still, as seen in FIG. 2 or 4, the maximal number of channels may be limited by the electrical contacts 41-44a of the chip and the ports of a processing element 102 of an external monitoring module 100.

In embodiments (not shown), up to seven channels may be arranged on a same chip, depending on limits imposed by the chip area and the external monitoring device 100; the larger the area the higher the cost.

Each channel requires at least two electrodes for the capacitance measurements, this including a ground electrode. Still, one may use one common ground electrode for all channels, and seven independent electrodes for seven channels in the above example. Note that for very conductive liquids such as PBS, the capacitance measured in one channel may impact measurements on another channel. However, such a phenomenon can be modeled and compensated for, if necessary.

The present embodiments mostly assume two main microchannels 11, 11a, without prejudice. Still, features of the present chips are essentially described in respect of one of the channels (channel 11) and its corresponding electrodes 21, 22, the other channel 12 being otherwise similar to the first 11 one.

In preferred embodiments, each electrode 21, 22 is patterned in-plane with the flow-path and alongside the flow-path. As it can be realized, patterning electrodes in-plane is easier to fabricate than electrodes in separate surfaces, e.g., a top and a bottom surface of a channel. Preferably, electrodes are fabricated level with the flow path surface 12 (or so as to exhibit minimal outcrops), to minimize the perturbation on the liquid flow. An in-plane design of the electrodes is nevertheless less perturbative than a sandwich configuration (top and bottom electrodes) as the liquid 5 may "see" more wetting surface (i.e., the surface of the flow path between the electrodes and the surface of the channel beyond the electrodes) without meeting edges or corners in the former case.

In variants, electrodes could be patterned on the sides of anisotropically-etched (e.g., Si) channels, so that longitudinal electrodes would form (tapered) walls contiguous with the (bottom) wall, thus forming a flow path. In that case, no electrode need be placed at the bottom of the channel (though additional electrodes may be provided, if necessary) or on the top.

That electrodes be provided in-plane or on tapered walls, the measured capacitance is believed to essentially involve double-layer capacitances, due to the electrical double layer at the liquid-electrode interface, see FIG. 4, inset. It is for instance found to be essentially proportional to the electrodes' widths w in practice, consistently with the known fact that a double-layer capacitance is known to scale with the area involved. Less significantly, the measured capacitance was otherwise found to slightly decrease as the inter-electrode gap g increases. Still, the double-layer capacitance contributions are the most significant, according to experiments conducted by the present inventors. Several other effects may further impact the measured capacitance, e.g., non-linear constant phase elements and/or complex impedance with the effect of charge transfer resistor, etc. Effects involved depend on the types of liquid and materials used for the electrodes. Still, present inventors have generally observed an approximate linear relation between the electrodes' surface area and the measured capacitance for liquids as typically used in microfluidics.

Accordingly, the (simplified) capacitance model depicted in the inset of FIG. 4 shows two double-layer components $C_{dl}$ for the capacitance (which adds to the dry capacitance $C_d$ of the electrode). According to what precedes, capacitance measurements are slightly impacted by charge transfer resistances $R_{ct}$, as well as the resistance $R_s$ of the sample (i.e., liquid). The resistance $R_s$, which is in series to $C_{dl}$, has a much lower impedance than that of $C_{dl}$ for common liquids used in microfluidic applications, therefore it can be neglected. $R_{ct}$, which is related to the electrochemical charge transfer reaction between the electrode surface and the electrolyte, may affect the voltage drop on the $C_{dl}$ when it is charged through an external resistor. However, this effect may be negligible, considering that $R_{ct}$ has typically a much higher resistance value than that of an external resistor.

Concerning now the dimensions: one the one hand, an electrode width that is too small leads to a too small capacitance, which results in losing precision. On the other hand, too wide electrodes affect the capillary flow as they have a different water contact angle than the chip surface and notably the flow path (which typically is a $SiO_2$ surface). Too wide electrodes would further give rise to too high capacitance values, which would prohibitory increase measurement times, as explained later.

With these considerations in mind, preferred dimensions for the electrodes are the following. In embodiments, each electrode 21, 22 has a width w between 10 and 500 µm. The gap g between the electrodes is between 10 and 1000 µm and is preferably larger than an electrode's width w, to minimize perturbations on the liquid flow. More preferably yet, each of the electrodes 21, 22 has a width between 30 and 160 µm, while the gap between the electrodes is preferably between 40 and 520 µm. For wide capillary pumps (e.g., wider than 5 mm), the gap between the electrodes could be increased and/or multiple longitudinal electrode pairs could be patterned so as to have an averaging effect.

The above dimensions allow the flow velocities to be most accurately measured, as present inventors realized. A preferred material for the electrodes is Pd. Other noble metals, like Au, Pt, could be used as well.

Each microchannel 11, 11a is preferably configured as a passive capillary pump for propelling liquid 5 therein. In particular, a microchannel 11 may comprises a lattice of capillary structures 32, the latter acting as a passive capillary pump 30, 30a. As seen in FIGS. 2 and 4, the electrodes 21, 22 extend across the lattice 30.

The lattice need not have translational symmetry (i.e., constant lattice parameters). On the contrary, capillary structures 32 may have varying lattice parameters, especially at the level of the electrodes 21, 22. E.g., depending on the liquid, materials and dimensions used, the areal density of capillary structures may be locally lowered to make room for the electrodes or, on the contrary, increased to compensate for the flow perturbation caused by the electrodes, if needed.

In variants to capillary structures, the surface of the flow path may already be wetting enough to act as a passive capillary pump 30, without capillary structures being needed at all. In all cases, passive capillary pumps are preferred, for reasons of portability, simplicity and cost. Still, the presence of passive pumping means does not preclude other active pumping and/or injection means, which may notably be involved while injecting and/or propagating the liquid 5. In (less preferred) alternatives, liquids may be moved by means of active pumping means only.

In other variants, other liquid control mechanisms can be integrated on the chip or inside the microfluidic structures, such as piezoelectric, magnetic, electroosmotic or electrowetting control mechanisms, etc. The electrodes for flow monitoring can then be used as a feedback for precise control of the flow rate. Such liquid control mechanisms could be used against the capillary pressure to adjust the liquid flow, e.g., to slow down the liquid flow or to support it for a faster flow.

If lattices of capillary structures 32 are used, then electrodes 21, 22 preferably extend across the lattice, along a median thereof, as depicted in FIG. 2. This allows for most accurately extrapolating measurements as to a local flow rate to an entire cross-section of a channel 11 in practice as the liquid front is least impacted by the side/edge effects (where clogging or bubbles may more likely form). This, in turn, allows the liquid volume present in a microchannel to be accurately estimated.

In embodiments, the electrical circuitry comprises electrical connectors 41-44; 41a-44a that are located at an edge of the chip 10, as depicted in FIG. 2. The chip 10 may further have a form factor that allows the chip 10 to be easily inserted in a monitoring device 100 (FIG. 4). As electrical connectors 41-44; 41a-44a are provided at an edge of the chip 10, they allow for direct plugging of the chip 10 upon insertion in the monitoring device 100.

The electrical connectors 41-44; 41a-44a are preferably configured as flat contact pads, as assumed in FIG. 2. Ideally, contact pads should also respect a standard (e.g., microSD card, etc.) for better electrical interfacing with peripheral equipment.

In variants, one may use "pogo-pin" spring-loaded contacts, which require less area than flat contact pads, so that more contacts can be added in this case. Pogo-pin contacts can be located anywhere on the chip, allowing for electrical connection of a socket from, e.g., a main surface of the chip.

Referring now more specifically to FIG. 4, and according to another aspect, the invention can be embodied as a microfluidic measurement system 1. The system 1 comprises a microfluidic chip 10 as described above. In addition, it comprises a flow monitoring device 100. The latter is configured so as to allow connection of the chip 10 therewith. For instance, and as seen just above, direct plugging of the chip 10 may be achieved thanks to appropriately configured electrical connectors 41-44; 41a-44a, upon insertion of the chip in the monitoring device 100.

The overall dimensions of the monitoring device 100 are preferably less than 20 mm×60 mm×160 mm, for ergonomic reasons, and more preferably less than 10 mm×30 mm×80 mm. In the latter case, the device 100 can advantageously fit under a standard microscope or a fluorescence reader designed for microscope slides.

In embodiments, the flow monitoring device 100 further comprises a data processing unit 102, e.g., a microcontroller. A suitable example of microcontroller is the ATMega32U4 microcontroller by Atmel® (8-bit AVR RISC-based microcontroller). The microcontroller can be appropriately connected and programmed to monitor the capacitance as measured via the electrical circuitry of the chip 10, in operation.

The data processing unit 102 may further comprise an analog-to-digital converter 105. For example, the ADC may be located inside a microcontroller such as mentioned above ("ATmega32U4"). The ADC is appropriately connected to a bus of the controller 102 to communicate data signals as needed for subsequent operations. Only one physical ADC may be needed, as one ADC may nevertheless be connected to different channels by suitable programming and pin connections. In variants, a microcontroller may have multiple ADCs for simultaneous analog-digital conversion from different channels.

The data processing unit 102 is typically programmed with low-level computer-program instructions. Interestingly, the clock frequency of the analog-to-digital converter may be increased, provided that the language used be sufficiently low-level. E.g., the frequency may be larger than or equal to 1 MHz, e.g., equal to 4 MHz. An example of pseudo-code is given later, in sect. 3.

Another parameter to take into consideration is the number of bits. The microcontroller may for example use a 10 bit ADC (or more generally an 8 to 20 bits ADC, or even more). All these parameters impact the eventual resolution of the capacitance measurements. Still, higher frequencies and number of bits would require more power. Yet, as the applications contemplated herein do not need very fast measurements, a reasonable trade-off can be found, to avoid using power demanding ADCs.

Optimizing the ADC clock frequency makes it possible to monitor down to 5 pF peak-to-peak variations, which may typically correspond to 10 μm resolution for the flow monitoring, depending on the dimensions of the channel and electrodes 21, 22, and the type of the liquid advancing in the channel.

Figure 3A:
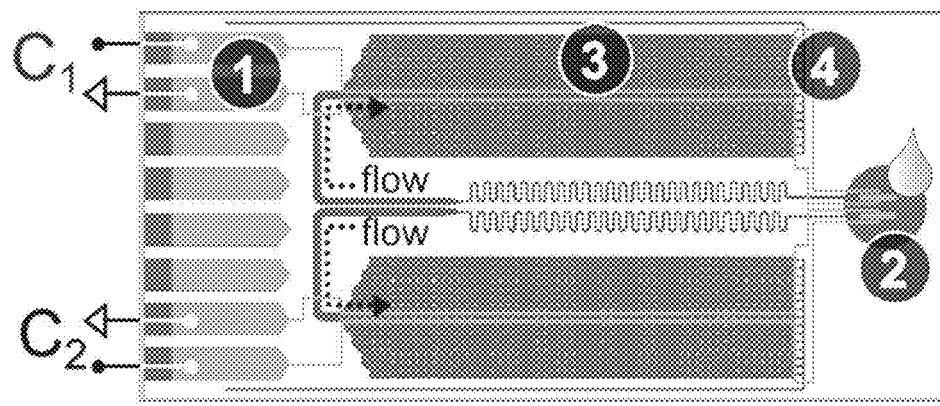
FIGS. 3A and 3B show a curve representing a capacitance as typically measured via the device of FIG. 2. Detectable events like chip detection, liquid detection and end-point detection are highlighted.
Figure 8:
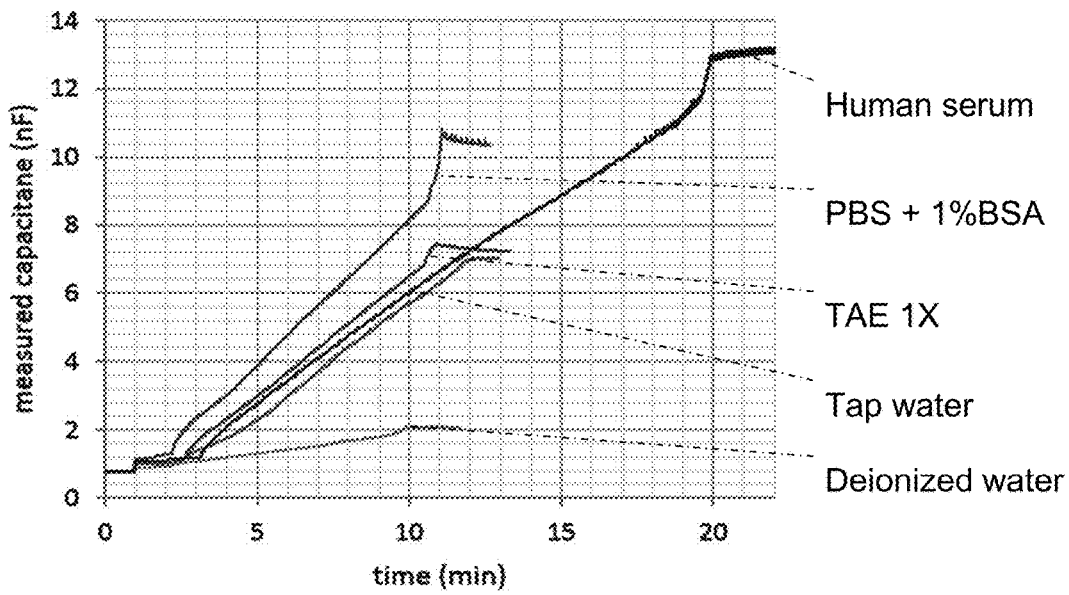
FIG. 8 is a plot representing capacitance curves of various liquids, as measured with devices according to embodiments.

Referring now to FIGS. 3A and 8: in embodiments, the flow monitoring device 100 used in the system 1 further comprises a data processing unit 102 that is configured to monitor the slope of the capacitance, beyond the capacitance itself. Monitoring the slope allows for detecting changes in the slopes, which in turn allows to detect events, as described below. In addition, the slope of the capacitance is per se interpretable as a position and/or a volume of liquid 5 as the latter continuously fills the microchannel, in operation. Moreover, measuring the slope further makes it possible to characterize the liquid, as distinct liquids have distinct slope signatures, as seen in FIG. 8.

As evoked above, the data processing unit 102 may, in embodiments, be configured to monitor changes in the slope of the capacitance, in operation. The changes in the slope (including abrupt changes) can then be interpreted as events, e.g., chip detection, liquid detection, end-point detection (where liquid reaches an end of the microchannel), etc. Such events typically precede or succeed insertion of the liquid in a microchannel and are useful for assisting the liquid operating the chip.

Changes in the slope of the measured capacitance can further be used to detect issues or defects of the chip (e.g., clogging, leakage, etc.).

In addition to the changes in the slope, the slope itself can also be used to deduct flow rate information, especially at the end of the operation, when the channels get completely filled by the liquid. The final flow rate information can for instance be used to calibrate the result of a bio-assay. Indeed, and even if the chip happens to work properly, there might be chip-to-chip variations in the measured flow (typically 5-10% variations). Thus, if the kinetics of the assay are known (e.g., because they were characterized beforehand), one can calibrate the result of the assay depending on the exact flow rate, so that errors due to flow rate variations can be compensated for.

Referring now to FIGS. 2 and 3A: in embodiments, the electrodes 21, 22 are suitably configured in the microchannel 11, 11a such as for the data processing unit 102 to be able to detect events from changes in the slope of the capacitance. Beyond issues in filling, the following events are notably detectable, in operation: (1) a detection of the chip 10 upon insertion thereof in the flow monitoring device 100; (2) a detection of a liquid 5 entering the microchannel; and (4) a detection of a liquid 5 reaching an end of the microchannel (end-point detection). The normal flow rate calculation regime (3) occurs between steps (2) and (4) in FIG. 3A.

To that aim, and as depicted in FIG. 2, the electrodes 21, 22 longitudinally extend in the microchannel portion 11 (or 11a), substantially from one end to the other of the channel portion 11 (11a). The electrodes may further be sharply bent at the ends of the channel portions. As it can be realized, a liquid entering the channel portion 11 (11a) from the bottom end or reaching the top end the channel portion 11 (11a) will accordingly produce a jump in the measured capacitance, which in turn allows a corresponding event to be detected. Other electrodes' configurations (e.g., having smoother bends, or only one electrode of the pair is bent, etc.) may be contemplated, which would nevertheless allow a change in the slope of the measured capacitance to be detected. In particular, in variants, the electrode may have wider or interdigitated sections to provide a unique signature of the position of the liquid, such as end-point detection at the end of the capillary pump.

Referring now specifically to FIG. 4, the measurement system 1 may further comprise, in embodiments, one or more graphical user interfaces (GUIs) 110, 200. The GUI(s) can be provided directly on the monitoring device 100 and/or on a separate device 200 (e.g., a computer or a smartphone). In all cases, the GUIs are connectable to the data processing unit 102. The unit 102 may thus instruct to provide appropriate feedback to the user, via the one or more GUIs 110, 200, based on the capacitance, the slope of the capacitance and/or changes detected in the slope of the measured capacitance.

Preferably, only the processing capability of the flow monitoring device 100 is used. In alternatives, part or all of the processing may delocalized, e.g., outsourced to a companion device 200 or even a remote server. A display 110 may be provided on the monitoring device and, if needed, information to be displayed thereon may be mirrored on the GUI of the companion device 200. To that aim, the latter 200 can be connected to the flow monitoring device 100, by way of a hard- or a wireless connection.

In addition to visual feedbacks, embodiments may further involve audio signals and/or vibration for warnings. During the measurements, the system 1 (including devices 10 and 100) may need to be kept in a closed chamber or inside a microscope, i.e., isolated from the user. Connecting the device 100 to a mobile phone 200 or a computer makes it possible to remotely warn the user (e.g., the phone can vibrate or a buzzer 108 is activated). In all cases, an alarm can be activated as soon as an issue is detected in the liquid flow. Accordingly, the user can take immediate action, e.g., the user need not wait for the filling to complete and can immediately proceed to change the defect chip.

Additional features of the chip, technical implementation details and other considerations as to possible fabrication processes are given in sect. 2. Technical details as to the microcontroller programming and capacitance measurements are given in sect. 3.

Figure 1:
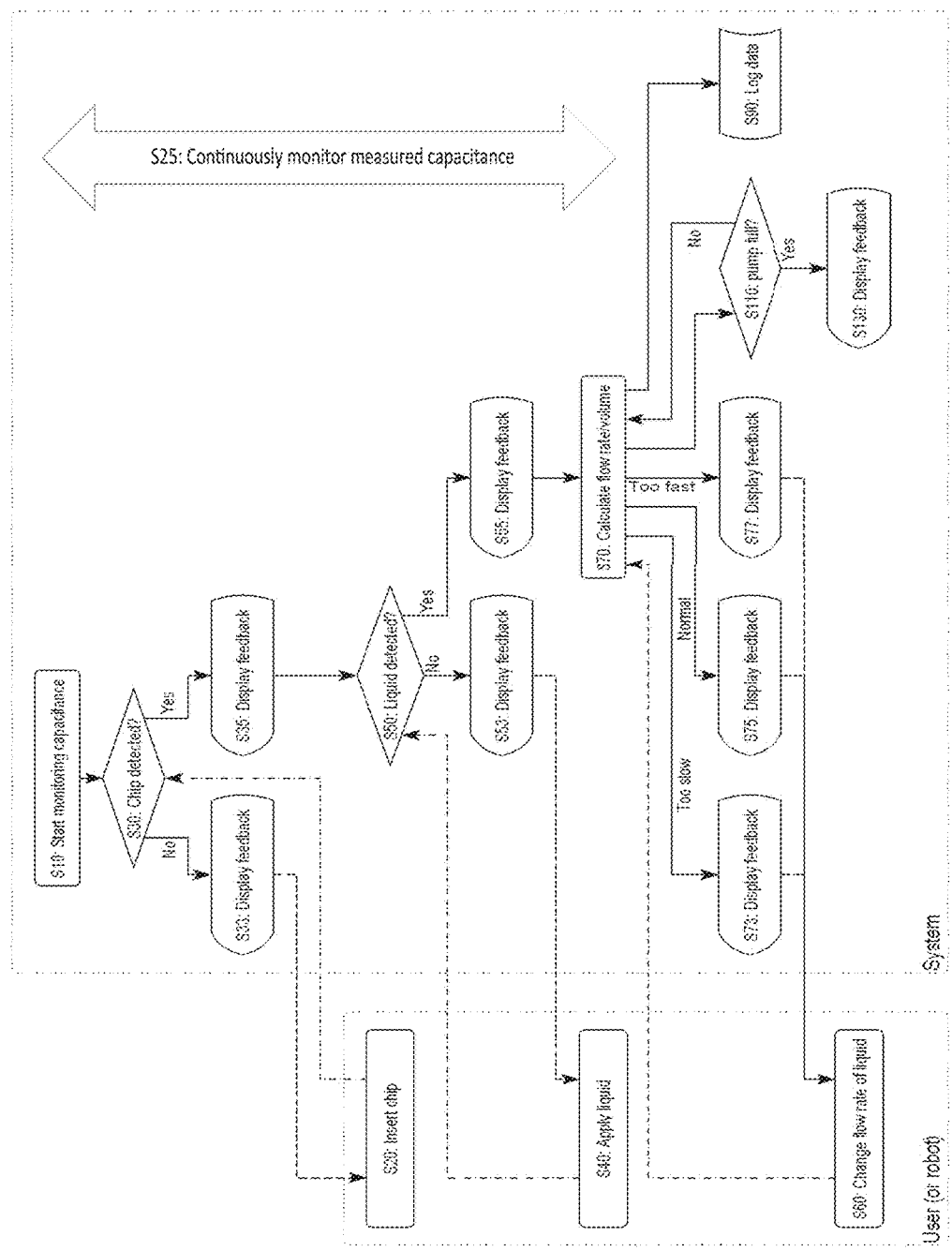
FIG. 1 is a flowchart illustrating high-level steps of a method for monitoring a liquid in a microfluidic chip, according to embodiments.
Figure 3B:
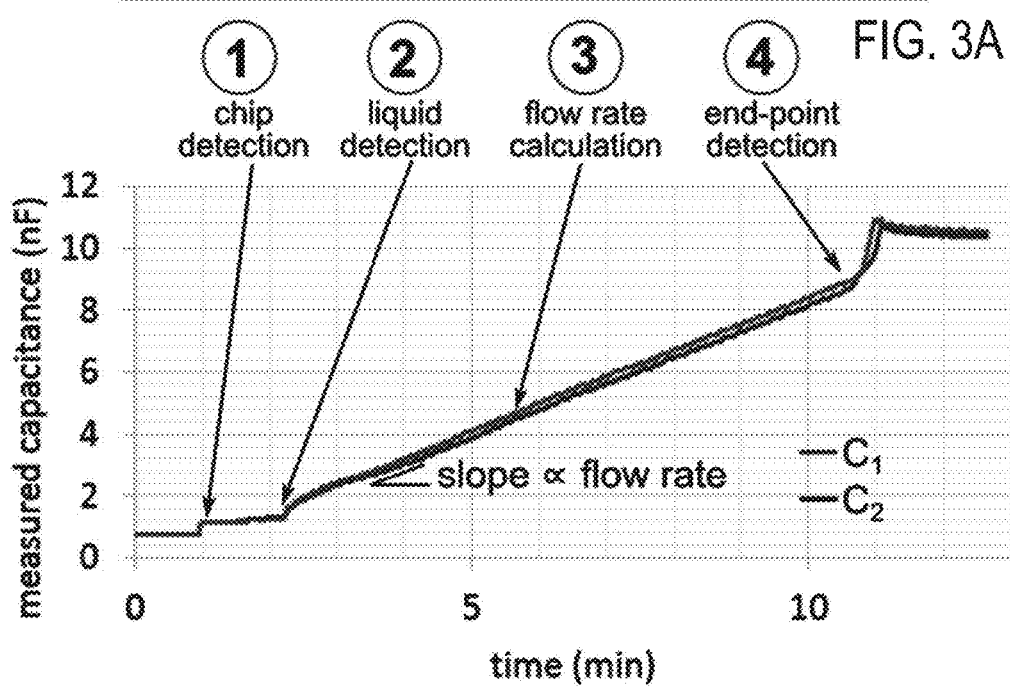

Next, referring to FIG. 1, and according to another aspect, the invention can be embodied as a method for monitoring a liquid 5 in a microfluidic chip 10 as discussed above, in reference to FIGS. 2-4. Essentially, this method revolves around monitoring S25 a liquid 5 continuously filling the microchannel of the chip 10. The monitoring S25 is performed by measuring a capacitance of the electrodes as the latter get wet by the liquid 5 that continuously fills the flow path 12, as a function of time. Capacitance measurements signals are provided from the electrical circuitry of the chip 10. Examples of resulting measurements are depicted in FIGS. 3A and 8.

As noted earlier, the microchannels 11, 11a may be configured as passive capillary pumps 30, 30a for propelling liquid 5 therein. As discussed earlier, the microchannels preferably comprise lattices of capillary structures 32, which act as passive capillary pumps, with the electrodes 21, 22 extending across the lattices.

Liquid 5 can be supplied S40, e.g., introduced using a pipette in the microchannels, e.g., via a loading pad 50 (FIG. 2), which is in fluid communication with each channel 11, 11a.

Once the liquid 5 has been introduced, the passive capillary pumps 30, 30a cause the supplied liquid 5 to spontaneously fill the microchannels 11, 11a. Meanwhile, the liquid flows can be continuously monitored S25, based on measurements signals from the electrical circuitry of the chip 10.

Thanks to preferred designs of the chip 10 and the device 100 as evoked above, peak-to-peak changes as small as 5 pF can be detected in the measured capacitance. Of course, larger changes may be detected as well, for example, a sudden jump when liquid is introduced. Peak-to-peak changes below 5 pF typically approach the noise level and therefore need not be accounted for.

In particular, a position and/or a volume of liquid 5 filling the microchannel 11 may be continuously calculated S70, while monitoring S25 the capacitance values. Preferably, the electrodes 21, 22 extend essentially along a median of a lattices 30, 30a, which in turn allows measurements as to a local flow rate to be extrapolated to an entire cross-section of the channels 11, 11a (and hence a volume to be most accurately estimated, if needed).

The flow rate can notably be calculated as follows. One may for instance measure a first capacitance value, C0, and then a second value C1, t seconds after e.g., t=10 s, C10, and calculate the rate (C1−C0)/t. Then, in order in order to estimate the flow rate from the measured capacitance, one needs to know electrical properties of the introduced liquid 5.

Two situations can be contemplated. In a first case, the user knows what type of liquid is being processed and therefore the electrical properties of the liquid can be fed in the monitoring device 100. Else, the system 1 may characterize the liquid, e.g., directly from the measured capacitance slope. In variants, the system 1 may measure electrical properties of the liquid thanks to electrodes provided in the loading pad 50 (FIG. 2). In other variants, one may provide electrodes in a channel section after the liquid loading pad 50 on the liquid path. In other variants, a side channel, which is not connected to the main flow path but connected to the loading pad, may be provided, so as to be used to characterize the electrical and fluidic properties of the liquid. In all cases, a liquid can be characterized, so as to infer properties of the liquid. Then, this information may be used to calculate the flow rate in the channels 11, 11a.

As evoked earlier, the microfluidic chip 10 may include several channels 11, 11a (e.g., two in the example of FIG. 2). The calculation step S70 may accordingly be based on, e.g., combine outcomes of respective capacitance measurements, i.e., measurements made via the electrical circuitry via each pair of electrodes 21, 22; 21a, 22a.

The continuous monitoring S25 may further comprise monitoring the slope of the capacitance, be it to enable detection S30, S50, S110 of changes in the slope of the capacitance. In general, all data of interest will be logged, S90. In particular, events corresponding to detected changes may be stored S90, e.g., events (1), (2) and (4) in FIG. 3A, to provide corresponding feedback to the user, as necessary. If the chip comprises an on-chip liquid control mechanism (e.g., based on magnetic, piezoelectric, electroosmotic, pneumatic, or electrowetting principles) or an external pump or a centrifugation system, the feedback can be used for precise tuning of the flow rate. As further reflected in FIG. 1, present methods may notably detect that: a chip was inserted (plugged) S20, S30 in the monitoring device 100; a liquid 5 has entered S50 a microchannel; and a liquid 5 has reached S110 an end of the microchannel 11. The data logged at step S90 need not necessarily be stored in a persistent memory.

In embodiments, visual feedback is provided S35, S55, S130 to the user along the process, via a graphical user interface 110, although other signals (audio, via buzzer, or vibration) could be used, instead of or in addition to visual signals. Once switched on, the device 100 starts S10 monitoring the capacitance. There, feedback can notably be provided S33, S35 prior to and after having detected S30 a chip that the user has inserted S20 (this creates a first jump (1) in the capacitance, see FIG. 3B). Similarly, feedback may be provided S53, S55 prior to and after having detected S50 liquid that the user has introduced S40 (which creates a second jump (2) in the capacitance, see FIG. 3B). In addition, other feedback may be provided S73, S75, S77 during the calculation step S70, informing (e.g., the user) about the fluid velocity (e.g., too slow, S73, normal, S75, or too fast, S77), prompting to take action S60.

Different scenarios can be contemplated here. In completely passive capillary systems, and if the flow is out of range, a user (or a robot) may throw the chip away. Now, if the flow is in the range, data obtained so far may be used to calibrate the assay. If, for example, on-chip or off-chip liquid control principles (e.g., electroosmotic, electrowetting, piezoelectric, pneumatic or magnetic control, etc.) are used, then the user, a device (e.g., a robot or some equipment of some sort), or the system itself may have control on the flow and take appropriate action. In another example, the user may decide to give the chip a chance, notwithstanding the warning (S73, S77), and wait some additional time. Indeed, a warning may have been triggered S73, S77 due to a minor defect in the pump and the flow rate get back to normal value. The user (respectively the system) could later decide (respectively inform) whether the temporary failure was critical for the assay result or not.

The fluid velocity impacts the capacitance (3) and the slope thereof, see FIGS. 3A and 8). Finally, if, as per calculations at step S70, the channels 11, 11a are found S110 to be full (end-point detection (4) in FIG. 3A), a corresponding feedback can be provided to the user, S130. Feedback provided at step S130 may for instance prompt the user to terminate the test, e.g., unplug the chip 10. In variants, this feedback S130 may indicate that the system is ready for assay measurements, e.g., for detecting an analyte using a fluorescence reader.

The feedback process as enabled in embodiments allows interactivity all along the process. Events can be detected (e.g., a chip is detected, S30-S35), prompting S35 to a next step S40 (introducing liquid) and leading, in turn, to the detection S50-S50 of a next event (liquid is detected), etc. For example, for applications where multiple pipetting steps are required, the system can guide the user on the next pipetting step and its timing. Information as to the flow rate calculation can furthermore be continuously reported to the user, S73-S77.

In further embodiments, multiple microfluidic devices may be run in parallel (e.g., in a clinical lab). In such cases, a whole monitoring system may be used in place of a single-chip monitoring device, the system monitoring several devices in parallel. When devices are ready for measurements, the monitoring system may provide a feedback such as "Device #1: flow OK; device #1 ready for measurement". Then, then the user (or an automated robot arm) may plug that device into an automatic reader. In such a scenario, the reader need not be utilized during the liquid (flow) filling phase, which may last up to 30 minutes or more in some cases. So, tens of (e.g., low-cost) microfluidic devices with flow monitoring option could be used, while only one (e.g., high-end, expensive) reader.

In still other embodiments, additional types of feedback may be provided. E.g., the system may be designed so as to warn the user that it is too late for measurements, e.g., because the user was unavailable for some time and has missed intermediate warnings, so that liquid in the channel may have dried and the results not valid anymore. Indeed, if liquid dries inside the channels (especially on a detection area) after some time, then this may alter the results.

The above embodiments have been succinctly described in reference to the accompanying drawings and may accommodate a number of variants. Several combinations of the above features may be contemplated. Examples are given in the next sections.

The flow path(s) 12, 12a are preferably capillary-driven, thanks to capillary pumps 30, 30a (which can be regarded as flow paths too) provided in fluid communication with the flow path or within the flow paths, and resulting in a capillary driven flow. Since the flow path is hydrophilic, a liquid fed into the flow path shall anyway wet the hydrophilic surface and advance in the flow path. A flow path is preferably provided in a closable microchannel, e.g., grooved in or structured on top of a surface of the chip, as discussed later. A flow path is "hydrophilic" inasmuch as it is defined by (at least) one hydrophilic surface. The flow path may nevertheless be defined by several surfaces, but not all these surfaces need be hydrophilic. Hydrophilicity of the flow path can be achieved by a combination of hydrophilic and hydrophobic surfaces or by having surfaces with various hydrophilic characteristics.

The use of passive capillary pumps allows for creating a more compact, autonomous and efficient system. Preferably, no active pumping (forced liquid injection, extraction by liquid pumping or centrifugation) is present, to achieve a more compact surface. In addition, the microfluidic chip does preferably not comprise any liquid connection to external devices e.g., via tubing ports, but rather is provided with just a liquid loading pad 50. For similar compactness reason, the chip does preferably not comprise any tank thereon.

A hydrophilic surface is defined in a microfluidic microchannel 11, 11a, and more precisely by one or more inner walls of a channel. This surface can be made of $SiO_2$, by way of thermal oxidation (from a Si wafer), which allows for high quality $SiO_2$ layers to be obtained. Still, $SiO_x$ layers may be obtained that convenes too, using low temperature deposition techniques, like sputtering, evaporation. However, $SiO_x$ surfaces shall likely have higher defect density and pinholes, which may impair electrical insulation properties as sought in applications. In variants, low-pressure chemical vapor deposition (LPCVD) of $Si_3N_4$ silicon nitride or atomic layer deposition (ALD) of dielectric layers, e.g., $Al_2O_3$, etc., can be contemplated too. ALD allows for high quality dielectric layers to be obtained. However, ALD is an expensive technique, with which thick layers, such as 50 nm or higher, may not be feasible.

Fabrication methods relying on anisotropic silicon etching may be employed for obtaining flush electrode surfaces 21, 22. Namely, the surface of an electrode (extending longitudinally along the flow path 12) that is exposed to liquid can be fabricated such as to be level, or essentially level, with a surrounding surface 12 in the flow path. In other words, electrodes preferably are arranged in a channel so as to be integrated within a superficial thickness of the surface of the channel that defines the flow path 12, the exposed surfaces of electrodes 21, 22 being essentially flush with the surrounding surface 12. This means that the misalignment between an exposed electrode surface and the surrounding surface is negligible with respect to the depth of the microchannel (preferably one to three orders of magnitude below or even less) or a typical thickness of a liquid 5 therein. For instance, methods are known, which allow misalignments are less than 20 nm, and even less than 10 nm, to be achieved, whereas the channel depth typically is between 10 and 20 μm. This minimizes surface topography and thus favors laminar flows, which may be advantageous to prevent incident in the liquid flow. Minimized surface topography is also advantageous to avoid pinning sites during the initial filling of a flow path by a liquid. This also reduces edge-defects on the electrodes and thus prevents spurious electric fields at the edges.

In variants such as evoked earlier, electrodes can be patterned on the tapered side walls.

Note that it is possible to have all electrodes drawn on the same mask layout and patterned at the same time through the same fabrication steps.

The liquid input 50 may for instance be a liquid loading pad 50, configured for loading liquid sample into the flow path, but could also be a microchannel, e.g., itself in communication with a liquid loading pad or another flow path, or any kind of liquid inlet (preferably a compact inlet).

The connection of electrodes to electrical contact pads may need to be carefully designed as it can substantially impacts the cost of chips. In this regard, the microfluidic chip may advantageously comprise electrical contacts mating with a socket. The contacts have preferably 500 μm width and 300 μm spacing, i.e. 800 μm pitch. The socket should preferably allow mechanical alignment of less than 200 μm to avoid short-circuits and wrong connections. As an example, HSEC8 type of edge connector from SAMTEC has 800 μm-pitch contacts and allows precise chip to socket alignment. For this socket, 4.5 mm long contact area is used for reliable electrical connection. Alternatively, sockets for microSD memory card (having, e.g., 8 contacts with 1.1 mm-pitch), can be used for chips having 3 mm long contact area. Chips can be designed to have final width of 100 μm less than the width of the socket opening (50 μm from each side less than the socket opening to allow easy placement without giving damage to the socket or the chip). Variations in the chip dimensions during chip dicing are expected to be within 50 μm. The contacts are placed on one side of the chip, preferably away from the loading pad (opposite side for instance). The number of contacts can be increased by repetition (constant pitch) as long as the chip dimension allows. The number of contacts can be decreased by sharing the ground electrode. Moreover, the same socket allows electrical connection to the backside of the chip in case a conductor or semiconductor, e.g. silicon, substrate is used and substrate biasing is required. In variants, "pogo-pin" spring-loaded contacts, which require less area than flat contact pads, could be used. Pogo-pin contacts can be located anywhere on the chip, allowing for electrical connection of a socket from, e.g., a main surface of the chip.

In a preferred embodiment, the chip measures 19.5×9.4 mm$^2$ and comprises a loading pad, a microchannel with embedded electrodes, a capillary pump, air vents, a cover film and electrical contacts mating with a card-edge socket. Silicon substrate is used to leverage the micromachining processes as well as the favorable properties of Si and SiO$_2$, such as channel etching with tapered sidewall profile, hydrophilicity of SiO$_2$ for capillary filling, thermal and chemical stability, mechanical robustness, compatibility of SiO$_2$ surface with many biomolecules, and well defined and reliable chemical composition.

In the fabrication process, channels are anisotropically etched in silicon using TMAH and electrically passivated by thermal oxidation. The electrodes are patterned by metal evaporation and lift-off after conformal coating and patterning of a single-layer photoresist. Prior to metal deposition, a short isotropic SiO$_2$ etching is introduced to assist lift-off and to recess the electrodes. The photolithography parameters are optimized to achieve at least a 5-μm minimum feature size in 20 μm deep trenches. Following the dicing and cleaning steps, a hydrophilic dry-film cover is laminated at 45° C. to seal the microfluidic structures. SEM inspection showed that the cover film perfectly tents over the channels and over the capillary pump. The electrodes showed minimized edge defects and very flat surface topography owing to the recessing step.

In other variants, electrodes are patterned on a flat Si surface having a SiO$_2$ passivation layer using a metal lift-off or a metal etching process. Microfluidic structures are then patterned using an additive process, such as photolithographic patterning of SU-8 or dry-film resist. Although not preferred, electrodes can also be patterned on the cover substrate (or film) and then bonded to the substrate carrying microfluidic structures using a chip or wafer bonding technique (e.g., film lamination, anodic bonding, direct bonding, thermoplastic bonding, adhesive bonding, etc.). In case there is already a chip functionality that requires electrodes (e.g., microheaters, electrodes for dielectrophoresis or electrowetting, or electrodes for amperometric, impedimetric, or electrochemical sensing, etc.), electrodes for liquid monitoring can be patterned together with the other electrode patterns or conductive layers in general.

Methods described herein can be used in the fabrication of microfluidic devices, notably wafer-based chips. The resulting chips can for instance be distributed by the fabricator in raw wafer form (that is, as a single wafer that has multiple unpackaged chips), as a bare die, or in a packaged form. In the latter case the chip is mounted in a single chip package (such as a plastic carrier) or in a multichip package. In any case the chip can then be integrated with other chips, or other microfluidic elements (tubing ports, pumps, etc.) even if applications to autonomous chips are preferred, as part of either (a) an intermediate product or (b) an end product.

In embodiments, the device 100 comprises a 3D-printed enclosure 106, housing a printed circuit board (PCB) 103 (FIG. 4). An ATmega32U4 microcontroller 102 is connected on the lower side of the PCB 103. Micro-USB receptor and plug 104 ensure power supply and communication. A buzzer 108 is mounted on top of the PCB 103, as well as a chip reader receptacle 107, having pads to provide electrical connectivity with the electrical circuitry of the chip 10 when inserted into the receptacle 107. A display 110 is further provided. All electronic components are connected to the microcontroller 102 via the PCB 103.

Note that the device 100 may further comprise (not shown) a battery and a Bluetooth module, where the USB port may be used for charging the battery. The footprint may however be unchanged, if, e.g., the battery and Bluetooth module are located below the PCB 103. Additional components may be provided on the PCB for wireless connectivity.

Figure 5:
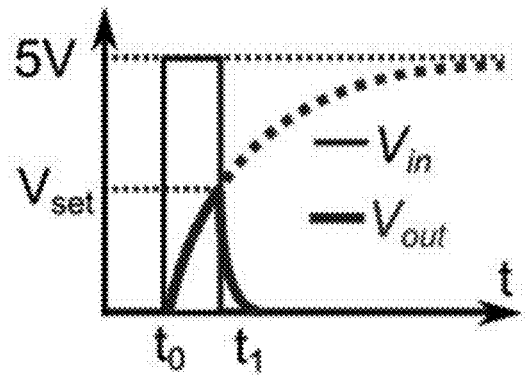
FIG. 5 is a plot representing a voltage during a charge and a discharge of a capacitor, as well as related quantities, as involved in a capacitance measurement, in embodiments.

The microcontroller comprises an ADC 105, which preferably works with a clock frequency in the range of 1 to 4 MHz or more. ADC measures voltage values continuously ("$V_{out}$", FIGS. 5 and 6) and the microcontroller waits until the value reaches that of $V_{set}$ (FIG. 5). The time needed to reach $V_{set}$ depends on the τ=RC time constant, which can, in present applications, typically be between 1 ms and 1 s, depending on the fixed resistor and the measured capacitance C. For example, a large capacitance makes it longer to reach to $V_{set}$. The maximum capacitance values are typically around 10 nF when the pump is full. This value can, however, depending on the size of the pump and electrodes. Setting the fixed resistor to 10 Mohm (megaohm) enables at least a couple of measurements per second with five times averaging. Considering that the capillary flow is usually slow in the capillary pump, a couple of measurements per second is enough to estimate the flow rate. If the capacitance gets too large, one measurement with averaging could take tens of seconds, which might be problematic for the precision of the measurement. In such cases, either the width of the electrode or the resistance of the fixed resistor can be reduced.

Figure 6:
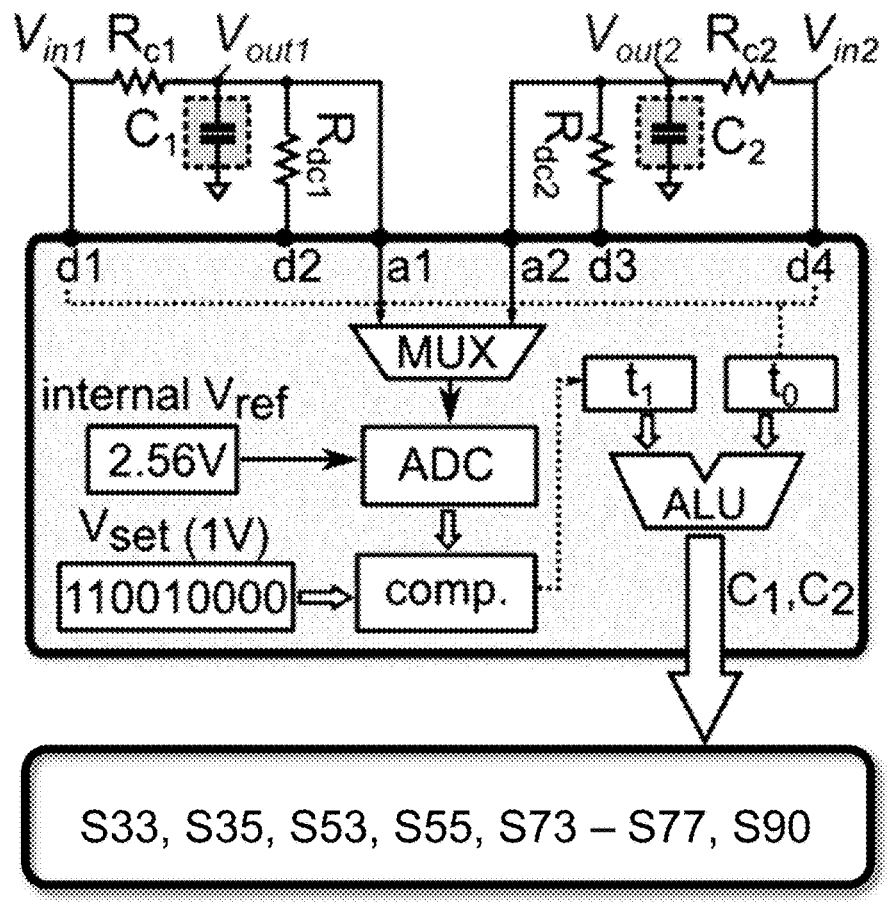
FIGS. 6 and 7 respectively show a diagram and a corresponding flowchart of a method for measuring a capacitance with a microcontroller, and from two microchannels, as involved in embodiments.
Figure 7:
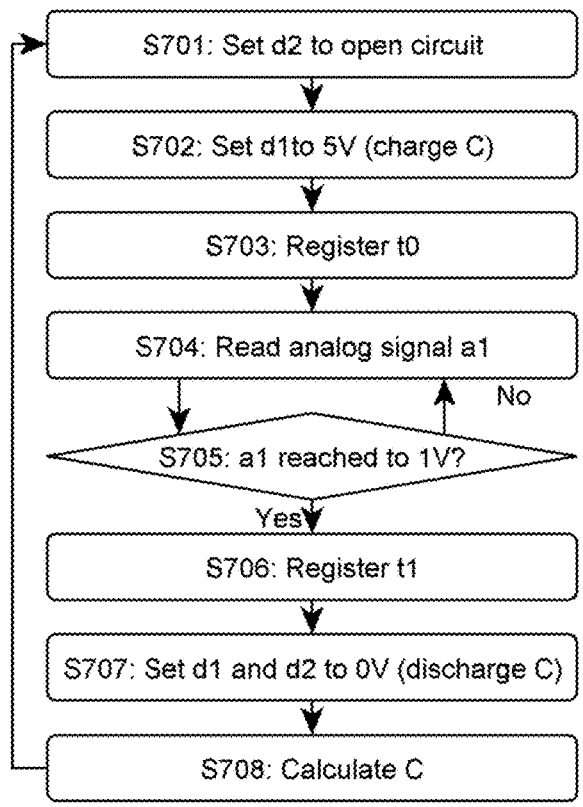

FIG. 5 generally represents a charge-discharge cycle for an unknown capacitor. Abbreviations used in FIGS. 6 and 7 are as follow:

Numerals 1 and 2 respectively refer to the first and second channels (except for times $t_0$ and $t_1$, which refer to distinct times, whose values are recorded during the operation, as in FIG. 5);

C denotes the unknown capacitance of the capacitor, i.e., comprising electrodes 21, 22 inside the microfluidic chip 10;

$R_c$ and $R_{dc}$ respectively refer to the charging and discharging resistors, which in each case is a physical resistor with a known value, typically a few Mohms (for $R_c$) or a few kohms (for $R_{dc}$), outside the microfluidic chip, on the circuit board 103);

$V_{in}$ denotes the voltage applied from the microcontroller to the electrical circuitry of the chip 10 to charge the unknown capacitor through $R_c$;

$V_{out}$ is the voltage measured from the unknown capacitor;

d1, d2, . . . dn denote digital pins of the microcontroller;

a1, a2, . . . an refer to analog pins of the microcontroller;

MUX stands for the multiplexer, through which the microcontroller may select the pins to be measured, thanks to suitable programming;

ADC denotes the analog-to-digital converter, as said;

Internal $V_{ref}$ is the reference voltage generated inside the microcontroller for the ADC operation;

$V_{set}$ is the set (threshold) value for the voltage on the capacitor;

comp. denotes a digital comparator; and

ALU is the arithmetic logic unit for calculations.

The operation of the ADC for capacitance measurements is now explained for one microchannel only. Multiple channels can be measured one after the other (in repeated sequences) or in parallel if the microcontroller has multiple ADCs.

A suitable technique is to measure the capacitance based on the time required to charge the capacitor to a set value using a known resistor. First, d2 (digital pin connected to the discharge resistor) is set to open circuit so that there is no direct current from d1 to d2 (step S701 in FIG. 7). A voltage is then applied S702 from d1 to charge the capacitor through $R_c$. The voltage level can be, e.g., 5, 3.3, 1.8 or 1.2V depending on the microcontroller used. Here, a value of 5V is assumed. There is a free running timer inside the microcontroller; when $V_{in}$ is set to 5V, the value $t_0$ of the timer is registered (in a buffer), S703. Then, one starts reading the value of $V_{out}$ using the ADC as the capacitor charges, S704. Each time the ADC produces S704 a value, this value is compared S705 to the set value (1V).

A very fast cycle is needed for read-compare operations. I.e., the ADC should be fast enough to not miss the set value. If read-compare operations are too slow, they would give rise to fluctuations on the measured value. This should especially be avoided when the capacitor is very small, e.g., as the capillary flow starts entering the pump. There the capacitor charges very fast so that ADC needs to capture the voltage values fast enough. For this reason, the ADC clock frequency may need to be increased to reduce the peak-to-peak variations. To that aim, low-level instructions may be needed.

When the voltage of the capacitor reaches to 1V, S705, the value of the timer is registered to another buffer, S706. Then, d1 and d2 are set to 0V (ground), S707, so that the capacitor discharges to 0V through $R_{dc}$ and becomes ready for the next reading. Here, $R_{dc}$ is much smaller than $R_c$, so it discharges much faster, because one wants the capacitor to be ready for the next reading as quickly as possible.

Then, ALU calculates S708 the capacitance value C from the known parameters ($R_c$, $V_{in}$, $V_{out}$, the latter being equal to $V_{set}$ at $t_1$, i.e., when stopping the operation) and recorded timer values ($t_0$ and $t_1$). Noting that $V_{out}=V_{in}(1-e^{-(t_1-t_0)/\tau})$, the capacitance can be calculated as:

$$C = \frac{-(t_1 - t_0)}{R\ln\left(1 - \frac{V_{out}}{V_{in}}\right)},$$

where the numerator involves measured quantities and the denominator set quantities. The fixed resistor, $R_c$, may have a manufacturing tolerance, e.g. 1%, therefore, the above formula may need to be calibrated for the exact measured value of the $R_c$. Alternatively, a variable resistor (a potentiometer) or a transistor can be used for precise calibration of the $R_c$. One can also plug a known capacitor instead of a microfluidic chip and calibrate the formula according to the known value.

In fact, the result need not be the exact value of a capacitor. Rather, it should merely be seen as a number increasing with the changing position of the liquid (as the latter fills the channel). Preferably though, the system may be calibrated so that all manufactured liquid monitoring systems give a same value for a same microfluidic chip. Otherwise there might be variations mostly due to the value of the fixed resistor.

In the above steps, $V_{set}$ is set to 1V to prevent any undesired electrochemistry (bubble formation, electrode corrosion, etc.). Several consecutive measurements may be made for a same channel; taking an average results in further reducing the noise.

Then, the same procedure can be repeated for other channels. Calculations steps for all channels may be interleaved.

Comments are in order. Preferably, the capacitor (so the electrodes) should not experience a potential that could result in electrochemical effects, as said. In addition, the measurements should preferably be:

Fast enough to monitor the flow of liquid, which is of particular concern when capacitance becomes largest, so that charging takes more time;

Precise enough to detect small variations, particularly at the beginning of the flow, when C is still small; and Low power enough so that it can be used for battery-powered, mobile applications.

Other techniques may be employed to measure the unknown capacitance, which may be more or less suited for small/large capacitances. If necessary, more advanced measurement techniques using auto-ranging (adaptive charging resistor, for example) may be involved.

According to a final aspect, the invention can be embodied as a computer program product for monitoring liquid 5 in a microfluidic chip 10 of a microfluidic measurement system 1 as described earlier. The computer program product comprising a computer readable storage medium having program instructions embodied therewith, where the program instructions are executable by one or more processing elements (preferably a microcontroller 102) of the flow monitoring device 100 of the system 1, to monitor a liquid continuously filling the microchannel of the chip, in operation.

As discussed in the previous subsection, low-level program instructions are preferably used, e.g., reflecting pseudo-code as used in FIG. 7.

More generally though, the computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions for carrying out operations of the present invention may notably be assembler instructions, machine instructions, or microcode. The computer readable program instructions may execute entirely on the device 100 or at least partly on a connected device 200. In embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations. It will be understood that each block of the flowchart illustrations, and combinations of blocks in the flowchart illustrations, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts.

The flowcharts in the Figures illustrate the architecture, functionality, and operation of possible implementations of devices, systems, methods, and computer program products according to various embodiments of the present invention. In this regard, each block in the flowcharts may represent a module, segment, or portion of instructions, which comprises one or more executable instructions for implementing the specified logical function(s). In some alternative implementations, the functions noted may occur out of the order noted in the figures. For example, two blocks shown in succession may, in fact, be executed substantially concurrently, or the blocks may sometimes be executed in the reverse order, depending upon the functionality involved. It will also be noted that each block of the flowcharts, and combinations of blocks, can be implemented by special purpose hardware-based systems that perform the specified functions or acts or carry out combinations of special purpose hardware and computer instructions.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, the present claimed microfluidic chips may be fabricated as a microfluidic probe.

What is claimed is:

1. A microfluidic chip comprising:
   at least one microchannel fillable with an electrically conductive liquid, the microchannel comprising:
      at least one pair of electrodes; and
      at least one liquid flow path defined between the electrodes, wherein each of the at least one pair of electrodes extends along the at least one liquid flow path and parallel to a direction of the liquid filling the microchannel, in operation, and
   an electrical circuitry connected to each of the electrodes and configured to continuously measure, via the electrodes, a capacitance of the electrodes being wet by the liquid continuously filling the at least one liquid flow path, as a function of time, in operation,
   wherein the at least one microchannel comprises a plurality of capillary portions, each capillary portion spaced apart from one another and each capillary portion including a lattice of individual capillary structures, the latter acting as a passive capillary pump, and
   wherein each electrode included in the at least one pair of electrodes is directly in contact with the electrically conductive liquid, and extends completely across every capillary portion among the plurality of capillary portions.

2. The microfluidic chip of claim 1, wherein each of the electrodes is patterned in-plane with the flow-path, alongside the flow-path.

3. The microfluidic chip of claim 1, wherein each of the electrodes has a width between 10 and 500 μm and a gap between the electrodes is between 10 and 1000 μm.

4. The microfluidic chip of claim 1, wherein
the chip comprises first and second microchannels, wherein the first microchannel comprises:
   a first pair of electrodes; and
   a first liquid flow path, the latter defined between the first pair of electrodes, said first pair of electrodes extending along the first liquid flow path and parallel to a direction of a liquid that fills the first microchannel, in operation,
wherein the second microchannel comprises:
   a second pair of electrodes; and
   a second liquid flow path, the latter defined between the second pair of electrodes, said second pair of electrodes extending along the second liquid flow path and parallel to a direction of the liquid that fills the second microchannel, in operation,
and wherein,
the electrical circuitry is connected to the first and second pair of electrodes and is configured to measure, via the first and second pair of electrodes, a capacitance of the liquid continuously filling the first and second flow path as a function of time, in operation.

5. The microfluidic chip of claim 1, wherein
the circuitry comprises electrical connectors located at an edge of the chip, the chip having a form factor allowing for insertion of the chip in a monitoring device, said electrical connectors configured so as to allow direct plugging of the chip upon insertion thereof in a monitoring device.

6. A microfluidic measurement system, comprising:
a microfluidic chip comprising:
   at least one microchannel fillable with an electrically conductive liquid, the microchannel comprising:
      at least one pair of electrodes; and
      at least one liquid flow path defined between the electrodes, wherein each of the at least one pair of electrodes extends along the at least one liquid flow path and parallel to a direction of the liquid filling the microchannel, in operation, and
   an electrical circuitry connected to each of the electrodes and configured to continuously measure, via the electrodes, a capacitance of the electrodes being wet by the liquid continuously filling the at least one liquid flow path, as a function of time, in operation; and
a flow monitoring device configured so as to allow electrical connection to the electrical circuitry of the microfluidic chip,
wherein the at least one microchannel comprises a plurality of capillary portions, each capillary portion spaced apart from one another and each capillary portion including a lattice of individual capillary structures, the latter acting as a passive capillary pump,
wherein each electrode included in the at least one pair of electrodes is directly in contact with the liquid, and extends completely across every capillary portion among the plurality of capillary portions, and
the circuitry comprises electrical connectors located at an edge of the chip, the chip having a form factor allowing for insertion of the chip in a monitoring device, said electrical connectors configured so as to allow direct plugging of the chip upon insertion thereof in a monitoring device.

7. The microfluidic measurement system according to claim 6, wherein
the flow monitoring device further comprises a data processing unit configured to monitor a capacitance of the electrodes being wet by a liquid continuously filling the flow path, as a function of time, as measured via the electrical circuitry of the chip, in operation, and wherein:
the data processing unit comprises an analog-to-digital converter; and
the data processing unit is programmed with computer-program instructions in a low-level language to monitor the capacitance, the language being low-level enough to allow for a clock frequency of the analog-to-digital converter that is larger than or equal to 1 MHz.

8. The microfluidic measurement system according to claim 6, wherein
the flow monitoring device further comprises a data processing unit configured to monitor a slope of a capacitance of the electrodes being wet by a liquid continuously filling the flow path, as measured via the electrical circuitry of the chip, in operation.

9. The microfluidic measurement system according to claim 8, wherein
the data processing unit is further configured to monitor changes in the slope of the capacitance, in operation.

10. The microfluidic measurement system according to claim 9, wherein
the electrodes are configured in the microchannel such as for the data processing unit to be able to detect, as part of said changes in the slope of the capacitance, one or more of the following events, in operation: a detection of the chip upon insertion thereof in the flow monitoring device; a detection of a liquid entering the microchannel; and a detection of a liquid reaching an end of the microchannel.

11. The microfluidic measurement system according to claim 9, further comprising:
a graphical user interface connectable to the data processing unit, and wherein,
the system is further configured to instruct to provide a feedback to the user, via the graphical user interface, and based on the slope of the capacitance and/or changes in the slope of a capacitance as measured via the electrical circuitry of the chip, in operation.

12. The microfluidic measurement system according to claim 11, wherein the system further comprises:
a mobile device, connectable to the flow monitoring device, the mobile device comprising said graphical user interface.

13. A method for monitoring a liquid in a microfluidic chip, the method comprising:
filling at least one microchannel with an electrically conductive liquid, the microchannel comprising a plurality of capillary portions, each capillary portion spaced apart from one another and each capillary portion including a lattice of individual capillary structures;
extending a pair of electrodes directly in contact with the liquid, and completely across every capillary portion among the plurality of capillary portions;
forming a liquid flow path between the electrodes, wherein each of the electrodes extends along the flow path and parallel to a direction of the liquid filling the microchannel, in operation;
connecting an electrical circuitry to each of the electrodes; and
supplying liquid in the microchannel and operating the microchannel as a passive capillary pump, using the plurality of capillary portions, to continuously propel the supplied liquid in the microchannel; and monitoring the liquid continuously filling the microchannel of the chip, by measuring, via the electrical circuitry of the chip, a capacitance of the electrodes being wet by the liquid continuously filling the flow path, as a function of time, while continuously propelling the supplied liquid in the microchannel.

14. The method of claim 13, wherein the at least one microchannel include two microchannels, each of the microchannels including the lattice of capillary structures, the latter acting as a passive capillary pump, and wherein, each microchannel includes disposed directly thereon a respective pair of electrodes, the pair of electrodes extending across the lattice, the method further comprising, while monitoring:

calculating a position and/or a volume of liquid filling the microchannel, from measurements made via the electrical circuitry.

15. The method of claim 13, wherein wherein calculating further comprises:

calculating at least one of a position and a volume of liquid filling the two microchannels based on outcomes of capacitance measurements made via the electrical circuitry via each pair of electrodes.

16. The method of claim 13, further comprising:

inserting the microfluidic chip in a flow monitoring device, so as to plug electrical connectors in the flow monitoring device.

17. The method according to claim 13, wherein monitoring comprises monitoring peak-to-peak changes of 5 pF in the measured capacitance.

18. The method according to claim 13, wherein monitoring further comprises monitoring a slope of the capacitance as the liquid continuously fills the flow path, based on signals from the electrical circuitry of the chip.

19. The method according to claim 18, further comprising, while monitoring the slope of the capacitance:

detecting changes in the slope of the capacitance, based on signals from the electrical circuitry of the chip.

20. The method according to claim 19, further comprising:

storing an event corresponding to a detected change in the slope of the capacitance, said event corresponding to one of: detecting that this chip was plugged in the flow monitoring device; detecting that the liquid has entered the microchannel; and detecting that a liquid has reached an end of the microchannel.

21. The method according to claim 20, further comprising:

providing a feedback to a user, via a graphical user interface, as to the stored event.

22. The method according to claim 21, further comprising:

detecting a further change in the slope of the capacitance as measured via the electrical circuitry of the chip after taking action in response to the feedback provided.

* * * * *